United States Patent [19]

Iwaki et al.

[11] 4,293,720

[45] Oct. 6, 1981

[54] PROCESS FOR PREPARATION OF HYDROPEROXIDES

[75] Inventors: Tetsuo Iwaki; Yukio Takahashi, both of Ohtake; Shuji Moriuchi; Hisamitsu Kaneko, both of Iwakuni, all of Japan

[73] Assignee: Mitsui Petrochemical Industries, Ltd., Tokyo, Japan

[21] Appl. No.: 146,080

[22] Filed: May 2, 1980

[30] Foreign Application Priority Data

May 9, 1979 [JP] Japan ............................ 54-55664

[51] Int. Cl.$^3$ ..................................... C07C 179/035
[52] U.S. Cl. ..................................... 568/575; 568/576
[58] Field of Search ........................... 568/575, 576

[56] References Cited

U.S. PATENT DOCUMENTS

| Re. 23,916 | 12/1954 | Lorand et al. | 568/575 |
| 2,655,545 | 10/1953 | Brüning et al. | 568/575 |
| 3,803,243 | 4/1974 | Brownstein et al. | 568/575 |

*Primary Examiner*—Werren B. Lone
*Attorney, Agent, or Firm*—Sherman & Shalloway

[57] ABSTRACT

Disclosed is a process for the preparation of hydroperoxides comprising liquid-phase oxidizing an aromatic compound having a secondary alkyl group with molecular oxygen in the presence of a basic aqueous solution and a copper compound catalyst, wherein an aqueous solution containing (A) cupric carbonate and (B) an alkali metal carbonate and/or an alkali metal bicarbonate is prepared outside the oxidation system and this aqueous solution is supplied to the oxidation system.

According to the process, even under basic conditions, inactivation of the catalyst owing to precipitation is prevented, and the intended aromatic hydroperoxide can be obtained at a high oxidation speed.

8 Claims, No Drawings

PROCESS FOR PREPARATION OF HYDROPEROXIDES

BACKGROUND OF THE INVENTION

(1) Field of the Invention

The present invention relates to a process for the preparation of hydroperoxides of aromatic compounds having a secondary alkyl group. More particularly, the present invention relates to an improvement of this process in which inactivation of a copper compound catalyst supplied to the reaction system owing to insolubilization thereof can be effectively prevented even under basic conditions.

(2) Description of the Prior Art

A process in which an aromatic compound having a secondary alkyl group, such as cumene, cymene, dimethylcumene or sec-butylbenzene, is oxidized with molecular oxygen to form a corresponding hydroperoxide has been previously known. Various processes for promoting this oxidation reaction by using heavy metal catalysts have been proposed, and certain effects have been attained by these processes. In most of these processes, a heavy metal catalyst is dissolved or suspended in the above-mentioned aromatic compound and oxidation is then carried out. However, they are still defective in various points. For example, the oxidation reaction speed is not sufficiently high and the selectivity to the intended hydroperoxide is low. Furthermore, a reaction vessel or the like is corroded by an organic acid formed as the by-product, and the heavy metal catalyst is inactivated because of insolubilization thereof. As means for preventing corrosion by the organic acid formed as the by-product, there may be considered a process in which oxidation is carried out in the co-presence of a basic aqueous solution. However, in such a basic aqueous solution, the heavy metal catalyst undergoes a chemical change and it is insolubilized, and there is a risk of inactivation of the catalyst. Accordingly, such a process has hardly been proposed. A process using an organic chelate compound of a heavy metal has been proposed in Japanese Patent Application Laid-Open Specification No. 142526/75 or No. 142527/75. However, preparation of this catalyst is not easy and this catalyst is very expensive. In the process disclosed in Japanese Patent Application Laid-Open Specification No. 142527/75, a precipitate is formed and the catalyst is inactivated unless the pH value of the aqueous phase is maintained below 7.5, as described in this Laid-Open Specification. Thus, the operation under basic conditions is remarkably limited. If an organic ligand having a high coordination power is used, the heavy metal ion can be kept water-soluble even at a high pH value. However, if a metal chelate compound containing such a strong organic ligand is used for the oxidation reaction, a problem arises in connection with the activity of the catalyst and there is a risk of reduction of the quality of the intended product by this ligand.

SUMMARY OF THE INVENTION

Under the above-mentioned background, we made researches on various heavy metal catalysts, and we found out a cheap catalyst which provides a sufficiently high oxidation speed, makes it possible to perform the operation within a broad pH range even under basic conditions while preventing precipitation of the catalyst and can be used repeatedly. More specifically, in accordance with the present invention, there is provided a process for the preparation of aromatic hydroperoxides comprising liquid-phase oxidizing an aromatic compound having a secondary alkyl group with molecular oxygen in the presence of a basic aqueous solution, wherein an aqueous solution containing (A) cupric carbonate and (B) an alkali metal carbonate and/or an alkali metal bicarbonate is supplied to the oxidation system.

DETAILED DESCRIPTION OF THE PREFERRED EMBODIMENTS

The aromatic compound to be oxidized is an aromatic compound having at least one secondary alkyl group directly bonded to the aromatic nucleus, such as an isopropyl or sec-butyl group, and this aromatic compound may have an alkyl group other than mentioned above, for example, a methyl or ethyl group, or a halogen as a substituent. As such aromatic compound, there can be mentioned, for example, cumene, m-cymene, p-cymene, m-diisopropylbenzene, p-diisopropylbenzene, p-ethylisopropylbenzene, 3,5-dimethylcumene, sec-butylbenzene and p-methyl-sec-butylbenzene. Especially good results are obtained when among these aromatic compounds, aromatic compounds which yield large quantities of carboxylic acids as by-products during the oxidation reaction and should therefore be oxidized in the presence of a basic aqueous solution, for example, those represented by the following formula:

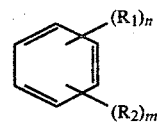

wherein $R_1$ stands for a secondary alkyl group having 3 to 4 carbon atoms, $R_2$ stands for a primary alkyl group having up to 4 carbon atoms, particularly a methyl group, and n and m are numbers of 1 or 2 with the proviso that the sum of n and m does not exceed 3, particularly cymene, dimethylcumene and diisopropyltoluene, are oxidized according to the process of the present invention.

In the oxidation process of the present invention, a basic aqueous solution is made present so as to neutralize an acid formed as the by-product and transfer it into the aqueous phase. The pH value of the aqueous phase is ordinarily maintained at 7 to 10, preferably 7.5 to 9. If the pH value is lower than 7, the acid formed as the by-product is not completely neutralized and the oxidation speed is reduced. If the pH value is higher than 10, the oxidation speed is reduced and there is a risk of insolubilization of the copper catalyst. In order to maintain the pH value within the above-mentioned range, it is preferred that an aqueous solution containing a carbonate of an alkali metal such as sodium or potassium and/or a bicarbonate of an alkali metal be appropriately supplied to the oxidation system. It is preferred that the concentration of the basic substance in the basic aqueous solution in the oxidation system be 0.3 to 1.8 mols per liter as the alkali metal, and that the oil phase/aqueous phase volume ratio in the oxidation system be from 98/2 to 50/50, especially from 95/5 to 70/30. Of course, the aqueous phase may be present in a larger proportion. In this case, however, no particular advantage can be attained but the volume of the oxidation tank should be increased.

Oxidation of the aromatic compound is performed by introducing molecular oxygen while contacting the oil phase intimately with the aqueous phase and preferably forming a water-in-oil suspension or emulsion. Pure oxygen gas or a gaseous mixture of pure oxygen and an inert gas, such as air, is used as the molecular oxygen. Intimate contact between the oil phase and the aqueous phase can be attained by introduction of molecular oxygen or by using ordinary agitating means such as a stirrer, a draft tube or a pump.

In the present invention, water-soluble cupric carbonate is used as the catalyst. A strong acid salt of copper is ordinarily known as a water-soluble salt of copper. If an aqueous solution of such a salt is directly supplied to the above-mentioned oxidation system, a part of the salt is precipitated in the oxidation system and the salt is not effectively utilized. The copper catalyst exerts a sufficient effect if it is incorporated in a minute amount, but if the copper catalyst is made present in a large amount, decomposition of the formed hydroperoxide is promoted. Accordingly, the copper concentration in the reaction system should be strictly adjusted. Furthermore, if insolubilization of a part of the copper catalyst is caused as pointed out hereinbefore, it becomes difficult to maintain an appropriate copper concentration in the reaction system. Accordingly, it is desired that the copper catalyst should be supplied in such a form that precipitation is not caused in the oxidation system. In the process of the present invention, the copper salt is dissolved in an aqueous solution of an alkali metal carbonate and/or an alkali metal bicarbonate and is supplied to the oxidation system in the form of cupric carbonate. It was found that if this procedure is adopted, formation of an insoluble copper salt is not caused and therefore, the copper concentration in the oxidation system can be strictly adjusted and the copper catalyst can be used repeatedly. In the visible spectrum of an aqueous solution of this cupric carbonate, an absorption band is observed at 740 nm, and in view of this fact and the result of the ESR measurement, it is estimated that this cupric carbonate has a structure represented by the formula $[Cu^{2+}(H_2O)_5]CO_3$. In principle, the above-mentioned aqueous solution of copper carbonate is prepared outside the oxidation system by incorporating an aqueous solution of a strong acid salt of copper into an aqueous solution of an alkali metal carbonate and/or an alkali metal bicarbonate. The solubility of copper carbonate differs according to the concentration of the carbonate and/or the bicarbonate and the mixing ratio of the carbonate and bicarbonate when they are used in combination. In order to attain a high copper carbonate concentration without formation of precipitates in preparing an aqueous solution of copper carbonate, it is preferred that the $CO_3$ concentration in the aqueous solution be at least 1 mol/l, especially 1.4 to 4.0 mols/l. Furthermore, it is preferred to use a mixture containing an alkali metal carbonate and an alkali metal bicarbonate at a molar ratio of from 8/2 to 4/6. Thus, it becomes possible to maintain the copper carbonate concentration at a level of at least 100 ppm as the copper atom in the aqueous solution. Ordinarily, an aqueous solution of copper carbonate having a concentration of at least 1 ppm, preferably 1 to 300 ppm, especially preferably 100 to 300 ppm, as the copper atom is prepared according to the above-mentioned method and is then used for the oxidation reaction.

The oxidation process of the present invention may be carried out batchwise, but is advantageously carried out in a continuous manner. More specifically, there is preferably adopted a process in which the aromatic compound, an aqueous solution of an alkali as the pH adjusting agent and the above-mentioned aqueous solution of copper carbonate are continuously supplied, an oxygen-containing gas is continuously blown and the product is continuously withdrawn from the oxidation system. The oxidation temperature is ordinarily 50° to 150° C., preferably 100° to 130° C. It is preferred that the aqueous solution of copper carbonate be supplied so that the copper concentration in the aqueous phase in the oxidation system is 0.01 to 5 ppm. It is estimated that the copper catalyst will be in the form of cupric carbonate in the oxidation system of the present invention, though the form differs to some extent according to the composition of the aqueous phase in the oxidation system.

After termination of the oxidation reaction, the aqueous phase is separated from the oil phase. The oil phase is supplied to the acid decomposition step for the preparation of phenols. Since copper carbonate is contained in the aqueous phase, it may be used again for the oxidation reaction after acids formed as by-products are removed according to need.

The present invention will now be described in detail with reference to the following Example that by no means limits the scope of the invention.

EXAMPLE 1

Preparation of Aqueous Solution Containing Cupric Carbonate and Alkali Metal Carbonate and/or Alkali Metal Bicarbonate Copper sulfate was added to an aqueous solution containing sodium carbonate and sodium bicarbonate at a mixing ratio shown in Table 1 at a $CO_3$ concentration of 1 mol/l, to form cupric carbonate. The solubility of cupric carbonate was determined to obtain results shown in Table 1.

TABLE 1

| Sodium Carbonate/Sodium Bicarbonate Molar Ratio | pH | Concentration (ppm) of Dissolved Copper |
|---|---|---|
| 10/0 | 11.5 | 160 |
| 8/2 | 10.1 | 230 |
| 6/4 | 9.7 | 210 |
| 4/6 | 9.4 | 180 |
| 2/8 | 9.2 | 160 |
| 0/10 | 8.1 | 160 |

From the results shown in Table 1, it is seen that a highest concentration of dissolved copper is obtained at a sodium carbonate/sodium bicarbonate molar ratio of 8/2 and when this molar ratio is in the range of from 8/2 to 4/6, the concentration of dissolved copper is higher than in the case where sodium carbonate or sodium bicarbonate alone is used.

Copper sulfate was added to an aqueous solution of sodium carbonate, an aqueous solution of sodium bicarbonate or an aqueous solution containing sodium carbonate and sodium bicarbonate at a mixing molar ratio of 6/4. The $CO_3$ concentration in each solution was as shown in Table 2. The concentration of dissolved copper was determined to obtain results shown in Table 2.

TABLE 2

| Carbonate Concentration (mol/l) | Concentration (ppm) of Dissolved Copper | | |
|---|---|---|---|
| | Sodium Carbonate | Sodium Bicarbonate | Sodium Carbonate and Sodium Bicarbonate |
| 0.01 | 200 | 300 | 150 |
| 0.05 | 1 | 10 | 3 |
| 0.1 | 5 | 0.9 | 15 |
| 0.5 | 30 | 30 | 170 |
| 1.0 | 160 | 160 | 210 |
| 1.5 | 240 | — | 370 |

From the results shown in Table 2, it is seen that the copper concentration is lowest when the carbonate concentration is about 0.05 mol/l.

Test of Precipitation of Mixture of Aqueous Solution of Cupric Carbonate with Cymene Hydroperoxide 10 Parts of an aqueous solution formed by dissolving copper sulfate at a concentration of 300 ppm into an aqueous solution containing sodium carbonate and sodium bicarbonate at a molar ratio of 6/4 and adjusting the pH value to 6 to 10 was added to 90 parts of a liquid reaction mixture obtained by oxidation of cymene, which contained 9.6% by weight of cymene hydroperoxide. In an $N_2$ atmosphere, the mixture was agitated at a reaction temperature of 100° C. for 3 hours under atmospheric pressure.

It was found that no precipitate of copper was formed when the pH value was in the range of from 6 to 10.

Then, to 10 parts of an aqueous solution containing 300 ppm of copper sulfate, the pH value of which was adjusted to 6 to 10 by addition of a small amount of a mixture of sodium carbonate and sodium bicarbonate, was added 90 parts of the same liquid oxidation reaction mixture as described above. The mixture was agitated in an $N_2$ atmosphere at a reaction temperature of 100° C. for 3 hours under atmospheric pressure. It was found that a part of copper was precipitated when the pH value was 8.3 or higher, and that at a pH value of 10, about 40% of charged copper was precipitated in the form of reddish brown cuprous oxide.

From the foregoing results, it will readily be understood that in the system where the hydroperoxide formed by the oxidation reaction is present, a good dissolution state of copper can be maintained if copper is added in the state where it is dissolved in an aqueous solution containing sodium carbonate and sodium bicarbonate.

Oxidation of Cymene

To a continuous oxidation vessel, cymene and an aqueous solution containing 10% by weight of sodium carbonate were supplied at rates of 90 parts per hour and 10 parts per hour, respectively. Air oxidation was carried out at a reaction temperature of 120° C. under a reaction pressure of 5 Kg/cm²-G. Copper sulfate was dissolved in an aqueous solution containing sodium carbonate and sodium bicarbonate at a molar ratio of 6/4 and having a $CO_3$ concentration of 1.5 mols/l, so that the Cu concentration was 200 ppm. This solution was fed to the oxidation vessel as the catalyst at such a rate that the copper concentration in the oxidation vessel was 0.15 ppm.

When the total hydroperoxide concentration in the oil phase reached 12.4% by weight, the reaction speed of converted cymene to the total hydroperoxide was 56 g/l.hr.

The oxidation was carried out under the same conditions as described above except that an aqueous solution of copper sulfate was used as the catalyst and was fed to the oxidation vessel at such a rate that the copper concentration in the oxidation vessel was 0.15 ppm.

When the total hydroperoxide concentration in the oil phase reached 12.4% by weight, the reaction speed of converted cymene to the total hydroperoxide was 47 g/l.hr.

From the foregoing results, it will readily be understood that a solution formed by dissolving copper sulfate in an aqueous solution of sodium carbonate and sodium bicarbonate has a higher effect as the oxidation catalyst than an aqueous solution of copper sulfate.

What we claim is:

1. A process for the preparation of aromatic hydroperoxides which comprises reacting an aromatic compound represented by the following formula:

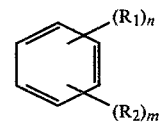

wherein $R_1$ stands for a secondary alkyl group having 3 to 4 carbon atoms, $R_2$ stands for a primary alkyl group having up to 4 carbon atoms, and n and m are numbers of 1 or 2 with the proviso that the sum of n and m does not exceed 3,
with a molecular oxygen-containing gas in the presence of a basic aqueous solution and a copper compound catalyst at a temperature of 50° to 150° C., wherein an aqueous solution containing (A) cupric carbonate and (B) at least one member of the group consisting of alkali metal carbonate and an alkali metal bicarbonate is prepared outside the oxidation system and said aqueous solution is supplied to the oxidation system, and the concentration of cupric carbonate in the aqueous phase in the oxidation system is maintained at 0.01 to 5 ppm as the copper atom.

2. A process for the preparation of aromatic hydroperoxides according to claim 1, wherein said aqueous solution is prepared by incorporating an aqueous solution of a strong acid salt of copper into an aqueous solution of an alkali metal carbonate and/or an alkali metal bicarbonate having a $CO_3$ concentration of at least 1 mol/l.

3. A process for the preparation of aromatic hydroperoxides according to claim 1, wherein said aqueous solution contains an alkali metal carbonate and an alkali metal bicarbonate at a molar ratio of from 8/2 to 4/6.

4. A process for the preparation of aromatic hydroperoxides according to claim 1, wherein said aqueous solution contains cupric carbonate at a concentration of 1 to 300 ppm as the copper atom.

5. A process for the preparation of aromatic hydroperoxides according to claim 1, wherein the liquid phase oxidation is carried out by agitating the oil phase containing the aromatic compound and the basic aqueous phase while maintaining the pH value and basic substance concentration of the aqueous solution phase at 7 to 10 and 0.3 to 1.8 mols/l as the alkali metal, respectively, adjusting the oil phase/aqueous phase volume ratio to from 98/2 to 50/50 and maintaining the concentration of the copper compound catalyst in the aqueous phase at 0.01 to 5 ppm as the copper atom.

6. A process for the preparation of aromatic hydroperoxides according to claim 1, wherein $R_2$ is a methyl group.

7. A process for the preparation of aromatic hydroperoxides which comprises feeding to the oxidation system (I) an aromatic compound represented by the following formula:

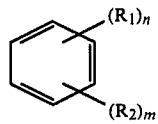

wherein $R_1$ stands for a secondary alkyl group having 3 to 4 carbon atoms, $R_2$ stands for a primary alkyl group having up to 4 carbon atoms, and n and m are numbers of 1 or 2 with the proviso that the sum of n and m does not exceed 3,
(II) an aqueous solution of a basic compound of an alkali metal as the pH adjusting agent and (III) an aqueous solution containing (A) cupric carbonate and (B) at least one member of the group consisting of an alkali metal carbonate and an alkali metal bicarbonate, blowing oxygen into the oxidation system while agitating the oil phase containing the aromatic compound and the aqueous solution phase containing the basic substance, performing oxidation of the aromatic compound at a temperature of 50° to 150° C. while maintaining the pH value and basic substance concentration of the aqueous solution phase at 7 to 10 and 0.3 and 1.8 mols/l as the alkali metal, respectively, adjusting the oil phase/aqueous phase volume ratio to from 98/2 to 50/50 and maintaining the copper compound catalyst concentration in the aqueous phase in the oxidation system at 0.01 to 5 ppm as the copper atom, withdrawing the reaction product from the oxidation system and separating the formed aromatic hydroperoxide therefrom.

8. A process for the preparation of aromatic hydroperoxides according to claim 1 or 7 wherein the aromatic compound is selected from the group consisting of cymene, dimethylcumene and disopropyltoluene.

* * * * *